US009919987B1

(12) United States Patent
Zhan et al.

(10) Patent No.: US 9,919,987 B1
(45) Date of Patent: Mar. 20, 2018

(54) NAPHTHENE RING OPENING OVER SELF-SUPPORTED MULTI-METALLIC CATALYSTS

(71) Applicant: Chevron U.S.A. Inc., San Ramon, CA (US)

(72) Inventors: Bi-Zeng Zhan, Albany, CA (US); Alexander Kuperman, Orinda, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/358,248

(22) Filed: Nov. 22, 2016

(51) Int. Cl.
| | |
|---|---|
| *C07C 5/31* | (2006.01) |
| *B01J 27/051* | (2006.01) |
| *C07C 5/27* | (2006.01) |
| *C07C 5/22* | (2006.01) |

(52) U.S. Cl.
CPC ............. *C07C 5/31* (2013.01); *B01J 27/0515* (2013.01); *C07C 5/22* (2013.01); *C07C 5/27* (2013.01); *C07C 5/2732* (2013.01); *B01J 27/051* (2013.01); *C07C 2527/051* (2013.01)

(58) Field of Classification Search
CPC ........... C07C 5/31; C07C 5/2732; C07C 5/27; C07C 5/22; B01J 27/051; B01J 27/0515
See application file for complete search history.

(56) References Cited

U.S. PATENT DOCUMENTS

| | | | |
|---|---|---|---|
| 3,617,511 A | 11/1971 | Jenkins et al. | |
| 5,345,026 A | 9/1994 | Chang et al. | |
| 5,763,731 A | 6/1998 | McVicker et al. | |
| 5,811,624 A | 9/1998 | Hantzer et al. | |
| 6,589,416 B2 | 7/2003 | Baird, Jr. et al. | |
| 6,623,625 B2 | 9/2003 | Baird, Jr. et al. | |
| 6,623,626 B2 | 9/2003 | Baird, Jr. et al. | |
| 6,683,020 B2 | 1/2004 | Baird, Jr. et al. | |
| 7,838,696 B2 * | 11/2010 | Maesen ................. | B01J 23/002 556/28 |
| 9,199,224 B2 | 12/2015 | Han et al. | |
| 2007/0138054 A1 * | 6/2007 | Palmer .................. | C10G 27/04 208/33 |
| 2014/0066296 A1 * | 3/2014 | Han ...................... | B01J 27/043 502/220 |

OTHER PUBLICATIONS

Barker et al., Petroleum, Kirk-Othmer Encyclopedia of Chemical Technology, 2005, John Wiley & Sons, Inc.*
(Continued)

*Primary Examiner* — In Suk C Bullock
*Assistant Examiner* — Youngsul Jeong
(74) *Attorney, Agent, or Firm* — Terrence M. Flaherty (57) ABSTRACT

A process is disclosed for opening naphthenic rings of naphthenic ring-containing compounds. Naphthene ring opening is achieved using a self-supported mixed metal sulfide catalyst comprising nickel sulfide, molybdenum sulfide, tungsten sulfide and an organic complexing agent. The catalyst is characterized as having a composition of metal components, in terms of molar ratios; as follows: $0.25 \leq Ni/(Ni+Mo+W) \leq 0.80$; $0 < Mo/(Ni+Mo+W) \leq 0.25$; $0.12 \leq W/(Ni+Mo+W) \leq 0.50$; and $1.5 \leq W/Mo \leq 3.0$.

13 Claims, 4 Drawing Sheets

(56) References Cited

OTHER PUBLICATIONS

McVicker et la. (Selective ring opening of naphthenic molecules, 2002, Journal of catalysis, 210, 137-148) (Year: 2002).*
G.B. McVicker, M. Daage, M.S. Touvelle, C.W. Hudson, D.P. Klein, W.C. Baird Jr., B.R. Cook, J.G. Chen, S. Hantzer, D.E.W. Vaughan, E.S. Ellis, and O.C. Feeley "Selective Ring Opening of Naphthenic Molecules" J. Catal. 2002, 210, 137-148.
M. Perez De La Rosa, S. Texier, G. Berhault, A. Camacho, M.J. Yacaman, A. Mehta, S. Fuentes, J.A. Montoya, F. Murrieta and R.R. Chianelli "Structural Studies of Catalytically Stabilized Model and Industrial-Supported Hydrodesulfurization Catalysts" J. Catal. 2004, 225, 288-299.

\* cited by examiner

NAPHTHENE RING OPENING OVER SELF-SUPPORTED MULTI-METALLIC CATALYSTS

TECHNICAL FIELD

The present disclosure relates to a process for selectively opening naphthenic rings of naphthenic ring-containing feeds using self-supported mixed metal sulfide catalysts.

BACKGROUND

Hydrocracking of hydrocarbon feedstocks is often used to convert lower value hydrocarbon fractions into higher value products, such as conversion of vacuum gas oil (VGO) feedstocks to various fuels and lubricants. Typical hydrocracking reaction schemes can include an initial hydrotreatment step, a hydrocracking step, and a post-hydrocracking step, such as dewaxing or hydrofinishing. After these steps, the effluent can be fractionated to separate out a desired diesel fuel and/or lubricant oil base oil.

Most petroleum and hydrocarbon streams derived from crude contain naphthene and aromatic compounds. Naphthenes and aromatics are considered undesirable in some product streams as they may degrade product quality.

Distillate fuels typically contain paraffins, naphthenes, and aromatics. For fuel quality parameters such as cetane number, gravity and emissions, paraffins are the most desirable components, followed by naphthenes, followed by aromatics. The least desirable are multi-ring aromatic compounds. While various refinery processes produce distillate fuels, these processes are typically limited in their capability to produce high quality distillate fuel and/or high yields of distillate fuel. For example, conventional hydrogenation processes saturate aromatic rings to naphthenes, thereby increasing the cetane number and increasing the API gravity (lower density). The disadvantage of hydrogenation alone is that naphthenes have generally lower cetane values and are more dense than paraffins having substantially the same number of carbon atoms. The greater density of naphthenes results in reduced volume of the distillate fuel blend relative to a composition containing similar concentrations of paraffins instead of naphthenes. Similarly, multi-ring naphthenes are generally more dense and have lower cetane values than single-ring naphthenes having substantially the same number of carbon atoms. In addition, naphthenes can be converted to aromatics via oxidation reactions. Since combustion of naphthenes in fuels occurs under oxidizing conditions, there is the potential for naphthenes to revert to aromatics under combustion conditions, thus further reducing fuel quality.

For lubricant basestocks, multi-ring naphthenes can present drawbacks with regard to viscosity index (VI) and oxidative stability. Multi-ring naphthenes tend to have poor VI compared to paraffinic molecules. In addition, such naphthenes typically have poor oxidation stability which is undesirable in a high temperature environment due to thermal breakdown and sludge formation. Aromatics generally have poor VI and oxidation stability properties as well. Multi-ring aromatics have very poor VI properties and are usually hydrogenated for environmental and health reasons.

Conventional hydrocracking catalysts that open naphthenic rings rely on high acidity to catalyze this reaction. Because hydrocracking with a highly acidic catalyst breaks both carbon-carbon and carbon-hydrogen bonds, the use of such a catalyst cannot be selective in just opening rings of naphthenic species without further cracking desired paraffins.

Conventional ring opening catalysts typically comprise at least one noble metal hydrogenation component dispersed on an acidic refractory oxide support. Some conventional processes employ supported iridium-containing catalysts for opening naphthene ring compounds. However, these catalysts are sensitive to high sulfur content feeds (e.g., >10 ppm sulfur).

The self-supported mixed metal sulfide catalysts of the present disclosure generally exhibit sulfur and nitrogen tolerance as well as high selectivity for ring opening of naphthenic compounds.

SUMMARY

In one aspect, there is provided a process for selective opening naphthene rings of naphthene ring-containing compounds in a feed stream, the process comprising: contacting a naphthene ring-containing feed stream under ring opening conditions with hydrogen and a self-supported mixed metal sulfide catalyst comprising nickel sulfide, molybdenum sulfide, tungsten sulfide and an organic complexing agent, thereby forming a ring-opened product having increased linear paraffin functionality relative to that of the feed stream; wherein the self-supported mixed metal sulfide catalyst is characterized as having a composition of metal components, in terms of molar ratios; as follows: (a) $0.25 \leq Ni/(Ni+Mo+W) \leq 0.80$; (b) $0 < Mo/(Ni+Mo+W) \leq 0.25$; (c) $0.12 \leq W/(Ni+Mo+W) \leq 0.50$; and (d) $1.5 \leq W/Mo \leq 3.0$.

DETAILED DESCRIPTION

Definitions and Abbreviations

"CAT" means catalyst average temperature.

"HCR" means hydrocracking.

"Hydrocracking" refers to a process in which hydrogenation and dehydrogenation accompanies the cracking/fragmentation of hydrocarbons, e.g., converting heavier hydrocarbons into lighter hydrocarbons, or converting aromatics and/or cycloparaffins (naphthenes) into non-cyclic branched paraffins.

"LV %" means liquid volume percent.

"Molybdenum sulfide" refers to $MoS_{2+e}$, where e may have a value between 0 and 1, and may further comprise carbide, nitride and/or sulfocarbide domains. $MoS_2$, as used herein, is by way of exemplification for molybdenum sulfide or $MoS_2$, in general and is not intended to exclude any molybdenum sulfide not represented by the formula.

"Naphthenes" are cycloparaffins having one or more cyclic rings. The rings may have 5 or more carbon atoms and may be substituted with substitutents such as alkyl groups of 1 to 20 carbons atoms. Naphthenes may also be polycyclic, i.e., containing multiple rings. Heavier petroleum fractions commonly include polycyclic naphthenes containing 2, 3, 4, 5 or more rings which may be fused.

"Self-supported catalyst" may be used interchangeably with "bulk catalyst" or "unsupported catalyst," meaning that the catalyst composition is not of the conventional catalyst form which consists of a catalyst deposited on a preformed shaped catalyst support. In one embodiment, the self-supported catalyst is formed through precipitation. In one embodiment, the self-supported catalyst has a binder incorporated into the catalyst composition. In another embodiment, the self-supported catalyst is formed from metal compounds and without any binder.

"SCFB" means standard cubic feet per barrel.

"Slab" refers to the crystal morphology of single particles or particle agglomerates of nickel sulfide.

The terms "edge" and "layer" are used herein as previously described by M. Perez de la Rosa et al. (*J. Catal.* 2004, 225, 288-299).

"Tungsten sulfide" refers to $WS_{2+e}$, where e may have a value between 0 and 1, and may further comprise carbide, nitride, sulfocarbide, and/or oxysulfide domains. $WS_2$, as used herein, is by way of exemplification for tungsten sulfide or $WS_2$, in general and is not intended to exclude any tungsten sulfide not represented by the formula.

"API gravity" is a measure of how heavy or light a petroleum liquid is compared to water, as determined by ASTM D4052.

"Kinematic viscosity" (KV) is a measurement in $mm^2/s$ of the resistance to flow of a fluid under gravity, as determined by ASTM D445.

"Polycyclic index (PCI)" refers to a measure of the content of compounds having several aromatic rings. PCI is useful in evaluating feedstocks for hydroprocessing. PCI is measured using UV-spectroscopy and is calculated as follows:

$$PCI=\{[Absorbance@385\ nm-(0.378\times Absorbance@435\ nm)]/115\times c\}\times 1000$$

where c is the original concentration of the sample in solvent in $g/cm^3$.

"Pour point" is a measurement of the temperature at which a sample will begin to flow under certain carefully controlled conditions, as determined by ASTM D5950.

"Viscosity index" (VI) is an empirical, unit-less number indicating the effect of temperature change on the kinematic viscosity of an oil. The higher the VI of the oil, the lower its tendency to change viscosity with temperature. VI is measured according to ASTM D2270.

"Surface area" is determined by $N_2$ adsorption at its boiling temperature. The BET surface area is calculated by the 5-point method at $P/P_0$=0.050, 0.088, 0.125, 0.163, and 0.200. Samples are first pre-treated at 400° C. for 6 hours in the presence of flowing, dry $N_2$ so as to eliminate any adsorbed volatiles like water or organics.

"Pore volume" is determined by $N_2$ adsorption at its boiling temperature at $P/P_0$=0.990. Samples are first pre-treated at 400° C. for 6 hours in the presence of flowing, dry $N_2$ so as to eliminate any adsorbed volatiles like water or organics.

All ASTM standards referred to herein are the most current versions as of the filing date of the present application.

Self-Supported Mixed Metal Sulfide Catalyst Compositions

Figure 1:
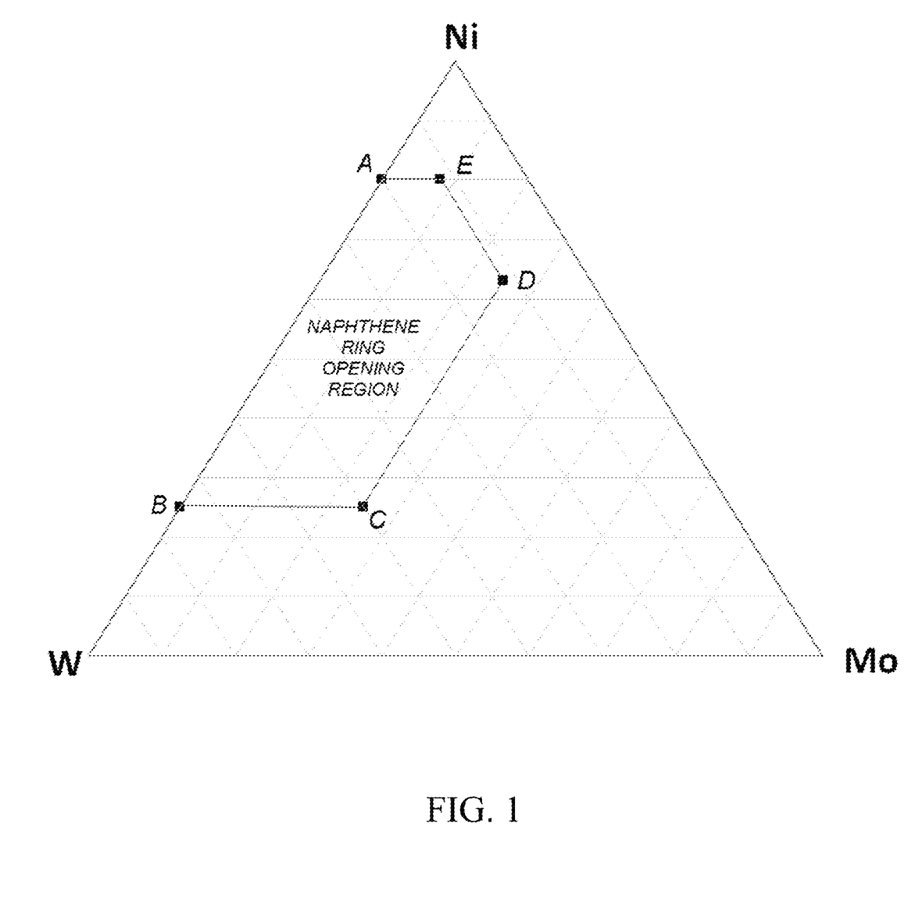
FIG. 1 is a ternary phase diagram showing contents of nickel, molybdenum, and tungsten as mol % on 100% metal basis in self-supported catalysts optimized to have naphthene ring opening activity, according to one embodiment.

In one embodiment, the self-supported mixed metal sulfide catalyst exhibits optimum naphthene ring opening when the relative molar amounts of nickel, molybdenum and tungsten are within a compositional range defined by five points ABCDE in the ternary phase diagram of FIG. 1, showing the element contents of nickel, molybdenum and tungsten in terms of their molar fractions. The five points ABCDE are defined as follows:
A (Ni=0.80, Mo=0.00, W=0.20);
B (Ni=0.25, Mo=0.00, W=0.75);
C (Ni=0.25, Mo=0.25, W=0.50);
D (Ni=0.63, Mo=0.25, W=0.12);
E (Ni=0.80, Mo=0.08, W=0.12).

Figure 2:
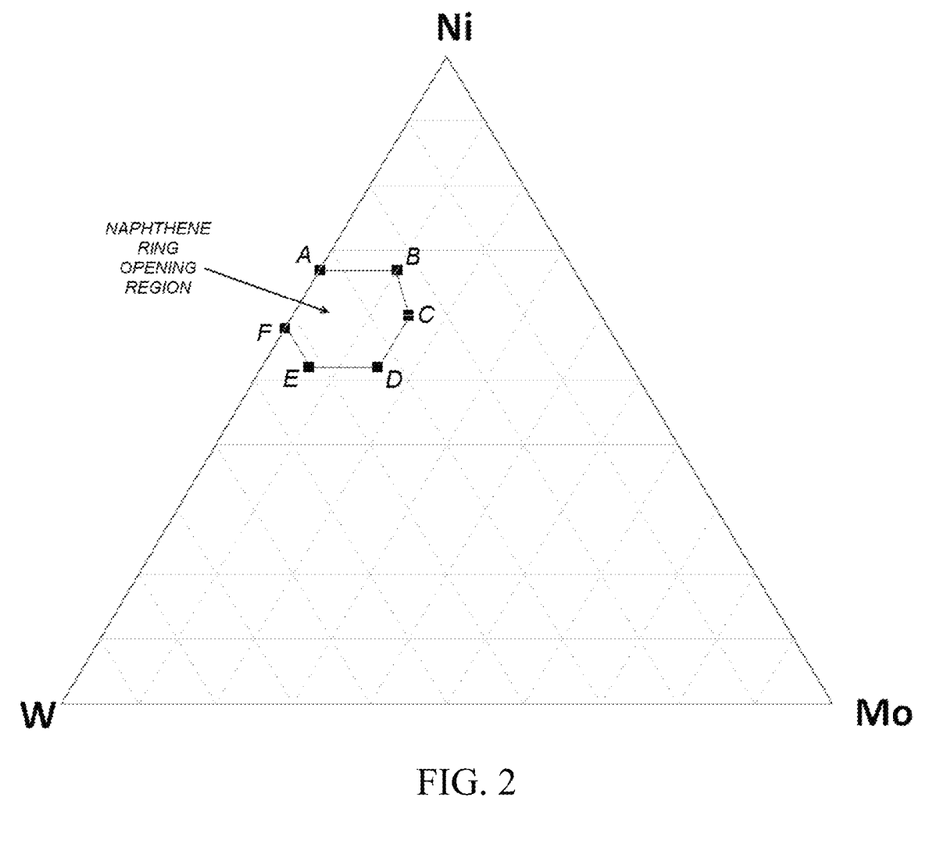
FIG. 2 is a ternary phase diagram showing contents of nickel, molybdenum, and tungsten as mol % on 100% metal basis in self-supported catalysts optimized to have naphthene ring opening activity, according to one embodiment.

In one embodiment, the self-supported mixed metal sulfide catalyst exhibits optimum naphthene ring opening when the relative molar amounts of nickel, molybdenum and tungsten are within a compositional range defined by six points ABCDEF in the ternary phase diagram of FIG. 2, showing the element contents of nickel, molybdenum and tungsten in terms of their molar fractions. The six points ABCDEF are defined as follows:
A (Ni=0.67, Mo=0.00, W=0.33);
B (Ni=0.67, Mo=0.10, W=0.23);
C (Ni=0.60, Mo=0.15, W=0.25);
D (Ni=0.52, Mo=0.15, W=0.33);
E (Ni=0.52, Mo=0.06, W=0.42);
F (Ni=0.58, Mo=0.00, W=0.42).

Figure 3:
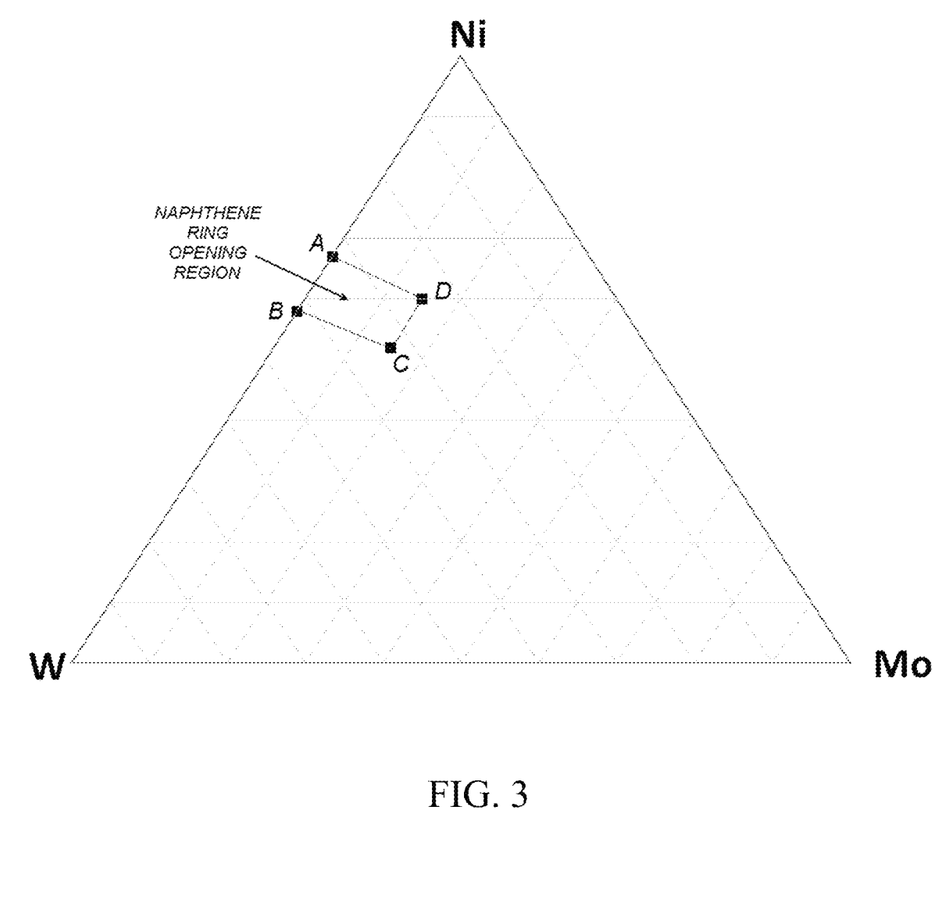
FIG. 3 is a ternary phase diagram showing contents of nickel, molybdenum, and tungsten as mol % on 100% metal basis in self-supported catalysts optimized to have naphthene ring opening activity, according to one embodiment.

In one embodiment, the self-supported mixed metal sulfide catalyst exhibits optimum naphthene ring opening when the relative atomic ratios of nickel, molybdenum and tungsten are within a compositional range defined by four points ABCD in the ternary phase diagram of FIG. 3, showing the element contents of nickel, molybdenum and tungsten in terms of their molar fractions. The four points ABCD are defined as:
A (Ni=0.67, Mo=0.00, W=0.33);
B (Ni=0.58, Mo=0.00, W=0.42);
C (Ni=0.52, Mo=0.15, W=0.33);
D (Ni=0.60, Mo=0.15, W=0.25).

In one embodiment, the molar ratio of metal components Ni, Mo and W in the self-supported mixed metal sulfide catalyst is in a range of:
$0.25 \leq Ni/(Ni+Mo+W) \leq 0.80$;
$0 < Mo/(Ni+Mo+W) \leq 0.25$;
$0.12 \leq W/(Ni+Mo+W) \leq 0.50$.

In one embodiment, the molar ratio of metal components Ni, Mo and W in the self-supported mixed metal sulfide catalyst is in a range of:
$0.50 \leq Ni/(Ni+Mo+W) \leq 0.75$;
$0 < Mo/(Ni+Mo+W) \leq 0.20$;
$0.15 \leq W/(Ni+Mo+W) \leq 0.45$.

In one embodiment, the molar ratio of metal components Ni, Mo and W in the self-supported mixed metal sulfide catalyst is in a range of:
$1.08 \leq Ni/(Mo+W) \leq 2.03$;
$0 < Mo/(Ni+W) \leq 0.18$;
$0.20 \leq W/(Ni+Mo) \leq 0.72$.

In one embodiment, the present self-supported mixed metal sulfide catalyst exhibits optimum performance in ring opening of naphthenes and sulfur and/or nitrogen tolerance at a W/Mo molar ratio in a range of 1.5 to 3.0 (e.g., 2.0 to 3.0, 2.0 to 2.9, 2.0 to 2.8, 2 to 2.7, 2.0 to 2.6, 2.0 to 2.5, 2.1 to 3.0, 2.1 to 2.9, 2.1 to 2.8, 2.1 to 2.7, 2.1 to 2.6, 2.1 to 2.5, 2.2 to 3.0, 2.2 to 2.9, 2.2 to 2.8, 2.2 to 2.7, 2.2 to 2.6, 2.2 to 2.5, 2.3 to 3.0, 2.3 to 2.9, 2.3 to 2.8, 2.3 to 2.7, 2.3 to 2.6, or 2.3 to 2.5).

Synthesis of Self-Supported Mixed Metal Sulfide Catalyst

The self-supported mixed metal sulfide catalysts are prepared from sources of nickel, molybdenum and tungsten in their elemental, compound, or ionic form ("metal precursors"). Any suitable nickel, molybdenum or tungsten metal reagent can be used to prepare metal precursor solutions.

Examples of nickel precursors include oxides or sulfides of nickel, organic compounds of nickel (e.g., nickel naphthenate, nickelocene), nickel carbonate, nickel chloride, nickel hydroxide, nickel nitrate and nickel sulfate.

Examples of molybdenum precursors include oxides or sulfides of molybdenum, organic compounds of molybdenum (e.g., molybdenum naphthenate), sulfur-containing organic compounds of molybdenum (e.g., molybdenum dithiocarbamates, molybdenum dithiophosphates), molybdic acid, alkali metal or ammonium molybdates (e.g., sodium molybdate, ammonium molybdate, ammonium heptamolybdate, ammonium tetrathiomolybdate), Mo—P heteropolyanion compounds (e.g., phosphomolybdic acid, sodium phosphomolybdate, ammonium phosphomolybdate), Mo—Si heteropolyanion compounds (e.g., 12-molybdosilicic acid), and molybdenum chlorides.

Examples of tungsten precursors include oxides or sulfides of tungsten, organic compounds of tungsten (e.g., cyclopentadienyl tungsten dihydride), tungstic acid, alkali metal or ammonium tungstates (e.g., sodium tungstate, sodium polytungstate, ammonium tungstate, ammonium metatungstate, ammonium tetrathiotungstate), W—P heteropolyanion compounds (e.g., 12-tungstophosphoric acid), and tungsten chlorides.

In one embodiment, the self-supported mixed metal sulfide catalyst is prepared by sulfiding an oxide or hydroxide catalyst precursor containing nickel, molybdenum and tungsten with a composition within inside the optimum range.

The catalyst precursor may be prepared in the presence of an organic complexing agent ("L"). Preferably, the organic complexing agent is a metal binding group or chelating agent. Preferably, the organic complexing agent is a bidentate ligand. In one embodiment, the organic complexing agent is suitable for forming metal-ligand complexes in solution.

Organic acids are a preferred class of organic complexing agent. In one embodiment, the organic complexing agent is an organic acid that contains a carboxylic acid functional group and at least one additional functional group selected from carboxylic acid, hydroxamic acid, hydroxo, keto, amine, amide, imine, or thiol. Examples of organic complexing agents suitable for use herein include glyoxylic acid, glycolic acid, diglycolic acid, thioglycolic acid, pyruvic acid, oxalic acid, malonic acid, maleic acid, succinic acid, lactic acid, malic acid, tartaric acid, citric acid, glycine, oxamic acid, glyoxylic acid 2-oxime, ethylenediaminetetraacetic acid, nitrilotriacetic acid, N-methylaminodiacetic acid and iminodiacetic acid. A preferred organic acid is maleic acid.

The amount of organic complexing agent used in the mixed solution should also be enough to form metal-organic complexes in the solution under reaction conditions. In an embodiment where the complexing agent is an organic acid, the ratio of carboxylic acid groups of the organic acids to metals can be at least 0.33, e.g., at least 0.5, at least about 1 (meaning that about the same number of carboxylic acid groups and metal atoms are present), at least 2, or at least 3. In another embodiment, the ratio of carboxylic acid groups to metals can be 12 or less (e.g., 10 or less, or 8 or less).

In another embodiment, the molar ratio used in the mixing solution of organic complexing agent to metals is 6:1 or less (e.g., 5.5:1 or less, 5:1 or less, or 4.5:1 or less). In yet another embodiment, the molar ratio used in the mixing solution of organic complexing agent to metals is 0.5:1 or more (e.g., 1:1 or more, or 1.5:1 or more, 2:1 or more, 2.5:1 or more, 3:1 or more, or 3.5:1 or more).

In one embodiment, molybdenum and tungsten precursors are first mixed in aqueous media with at least one organic metal complexing agent and the resulting solution is mixed with a nickel metal precursor under reacting conditions to form a slurry (a gel or suspended precipitate). It should be understood that the catalyst precursor composition is not limited to aqueous media; and the addition of the metal precursors/ligand can be in any order and can be mixed separately or together with the optional ligand. Suitable reaction conditions include a temperature of from 25° C. to 350° C. (e.g., 60° C. to 200° C.) and a pressure of from atmospheric to 3000 psig (101 kPa to 20.7 MPa), e.g., atmospheric to 1000 psig (101 kPa to 6.89 MPa). The pH of the reaction mixture can be changed to increase or decrease the rate of precipitation.

In one embodiment, the catalyst precursor is prepared from nickel, molybdenum, and tungsten metal precursors in the form of organometallic compounds of nickel, molybdenum, and tungsten, as starting materials, in amounts sufficient to form catalyst precursor containing nickel, molybdenum, and tungsten in the optimized compositional range. In another embodiment, the catalyst precursor is prepared by reacting at least a metal precursor (e.g., Ni, Mo, or W) with a single metal sulfide or a sulfur-containing organometallic compound such as molybdenum di-n-butyldithiocarbamate (MOLYVAN® A, Vanderbilt Chemicals, LLC).

After co-precipitation, the catalyst precursor is isolated or recovered in a liquid removal step using known separation processes (e.g., filtration, decantation or centrifugation) and then dried to further remove water. Drying can be effected at a temperature sufficient to remove water but not removal of any organic compounds, if present. Suitably, drying can be performed at 50° C. to 200° C. until a constant weight of the catalyst precursor is reached. It is preferred that a calcination step is not employed. In general, a calcination step involves the heating of the catalyst precursor above a temperature of 500° C. More preferably, the catalyst precursor is not subject in a subsequent step to a temperature exceeding 450° C., more preferably 350° C., more preferably 300° C., more preferably 250° C., more preferably 200° C. Within the meaning of the present invention, a catalyst or a catalyst precursor which is "non-calcined" is one which has not been subject to any one of the aforementioned calcination procedures.

Binders (or diluents), pore forming agents, and other additives known in the art can be incorporated into the catalyst precursor before being optionally shaped by processes known in the art (e.g., extrusion, pelleting or pilling). In one embodiment, the self-supported mixed metal sulfide catalyst or catalyst precursor is binderless, i.e., the particles of the self-supported catalyst or catalyst precursor are held together without the use of a conventional binder.

The catalyst precursor can be sulfided under conditions sufficient to at least partially convert the components of the catalyst precursor into a metal sulfide. Suitable sulfiding conditions include heating the catalyst precursor in an atmosphere containing a sulfiding agent (e.g., $H_2S$, dimethyl disulfide, inorganic or organic polysulfides, etc.) at a temperature ranging from 25° C. to 500° C., from 10 minutes to 15 days, and under a hydrogen-containing gas pressure. The sulfiding with a gaseous sulfiding agent such as $H_2S$ can be done ex-situ or in-situ (e.g., in the unit in which the catalyst will used for upgrading the hydrocarbon feed).

Characterization of the Self-Supported Mixed Metal Sulfide Catalyst

In one embodiment, the self-supported mixed metal sulfide catalyst containing nickel, molybdenum and tungsten may be characterized as being multiphasic, wherein the structure of the catalyst comprises five phases: (1) a molybdenum sulfide phase; (2) a tungsten sulfide phase; (3) a molybdenum tungsten sulfide phase; (4) an active nickel phase; and (5) a nickel sulfide phase.

The molybdenum, tungsten and molybdenum tungsten sulfide phases comprise at least a layer, with the layer comprising at least one of: (a) molybdenum sulfide and tungsten sulfide; (b) tungsten isomorphously substituted into molybdenum sulfide either as individual atoms or as tungsten sulfide domains; (c) molybdenum isomorphously substituted into tungsten sulfide either as individual atoms or as molybdenum sulfide domains; and (d) combinations of the aforementioned layers. The number of layers may range from 1-6.

Figure 4:
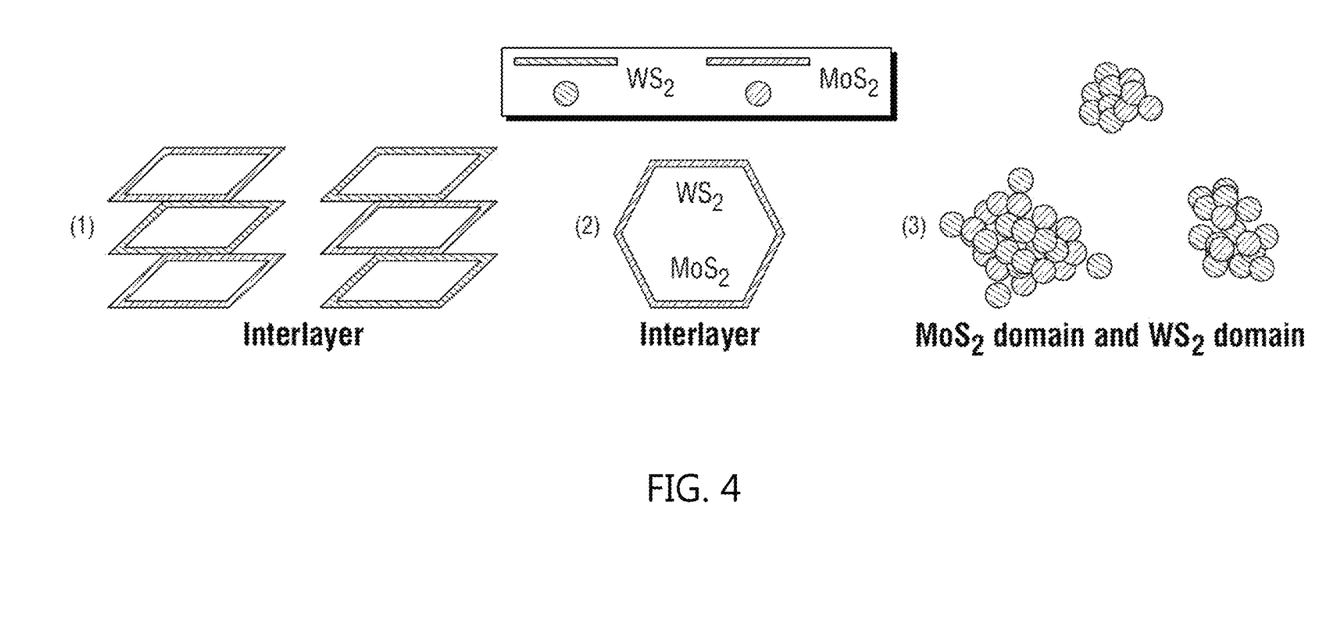
FIG. 4 is a pictorial representation of surface structure of the molybdenum tungsten sulfide phase of a self-supported mixed metal sulfide catalyst containing nickel sulfide, molybdenum sulfide, and tungsten sulfide in any form of: (1) intralayer atomic mixture; (2) inter-layer mixture of tungsten sulfide and molybdenum sulfide; and (3) a mixture of individual domains of tungsten sulfide and molybdenum sulfide.

In one embodiment, as illustrated in FIG. 4, the molybdenum tungsten sulfide phase is present as tungsten atomically substituted into molybdenum sulfide layers (or vice versa), forming an intralayer atomic mixture. In another embodiment, the molybdenum tungsten sulfide is present as an inter-layer mixture of tungsten sulfide and molybdenum sulfide. In yet another embodiment, the molybdenum tungsten sulfide phase is present as a mixture of individual domains of molybdenum sulfide and tungsten sulfide. The molybdenum tungsten sulfide phase can be observed by transmission emission microscopy (TEM) or X-ray diffraction (XRD).

The active nickel phase comprises: (a) at least one of atomic nickel (e.g., in the metallic state) and reduced nickel (e.g., nickel in an oxidation state lower than 2) substituted into the edge of the molybdenum tungsten sulfide phase and (b) $NiS_x$ nanoparticles (i.e., particles having a particle size on the nanometer scale, less than 1 micrometer) dispersed onto the molybdenum tungsten sulfide phase, where $0 < x \le 1$. The active nickel phase can be observed via TEM.

The nickel sulfide phase comprises slabs of at least one of $Ni_9S_8$ crystals and $Ni_3S_2$ crystals. The large nickel sulfide slabs serve as a support for the growth of molybdenum tungsten sulfide and stabilize the dispersion of active nickel on the surface of molybdenum tungsten sulfide. The nickel sulfide phase can be observed by XRD and TEM.

Without being bound by any theory, it is believed that the molybdenum tungsten sulfide phase acts as a support for the active nickel phase. In turn, the nickel sulfide phase stabilizes the dispersion of the molybdenum tungsten sulfide phase. The molybdenum tungsten sulfide phase envelops the nickel sulfide slabs so that the molybdenum tungsten sulfide layers exhibit a curved shape. Furthermore, the molybdenum tungsten sulfide phase develops defects in its lamellar crystalline structure on basal planes, creating cites associated with increased naphthene ring opening activity. It should be noted that different catalyst preparation routes, e.g., starting from decomposition of catalyst precursors in the form of organometallic compounds or co-precipitation of mixed metal oxohydroxide starting from oxygen-containing metal compounds may result in catalysts with a similar metal composition but different catalytic activities.

In one embodiment, the self-supported mixed metal sulfide catalyst exhibits reflection peaks indicative of the presence of molybdenum tungsten sulfide (according to the International Centre for Diffraction Data or ICDD), e.g., at 14.4°, 32.7°, 39.5°, 49.8° and 58.3° 2θ degree. In another embodiment the XRD pattern exhibits reflection peaks corresponding to the presence of a $Ni_3S_2$ phase (according to the ICDD), e.g., at 21.8°, 31.1°, 37.8°, 44.3°, 49.7°, 50.1° and 55.2° 2θ degree.

In one embodiment, the nickel sulfide phase exhibits lattice fringes with 4.60±0.5 Å spacing, corresponding to the [002] plane of $Ni_9S_8$ and with 2.87 Å±0.5 Å spacing, corresponding to the [110] plane of $Ni_3S_2$, as determined by TEM. These observations are indicative of crystalline nickel sulfide phases. They further suggest that the nickel sulfide phase serves as nucleation site (support) for the growth of the molybdenum tungsten sulfide phase which stabilizes the active nickel dispersion.

In one embodiment, the morphology of the self-supported mixed metal sulfide catalyst may consist of large (about 10 to 20 nm in one embodiment) nickel sulfide slabs ($Ni_2S_3$ or $Ni_9S_8$), with molybdenum tungsten sulfide layers enveloping these nickel sulfide slabs. The molybdenum tungsten sulfide layers may be arranged in stacks of about 1-4 layers with the majority of the layers being undulating. Active nickel sulfide ($NiS_x$) particles of varying size (1 to 20 nm) may reside at the edges of the molybdenum tungsten sulfide layers.

In one embodiment, the self-supported mixed metal sulfide catalyst has a Ni surface concentration to Ni bulk concentration ratio of at least 0.4 mol/mol and a W surface concentration to W bulk concentration ratio of at least 0.3 mol/mol, as determined by X-ray photoelectron spectroscopy (XPS). In another embodiment, the self-supported MMS catalyst has a Ni surface concentration to Ni bulk concentration ratio of at least 0.5 mol/mol and a W surface concentration to W bulk concentration ratio of at least 0.4 mol/mol, as determined by XPS.

In one embodiment, the self-supported mixed metal sulfide catalyst particles have a BET surface area of at least 20 $m^2/g$ (e.g., at least 40 $m^2/g$, at least 80 $m^2/g$, or at least 120 $m^2/g$).

In one embodiment, the self-supported mixed metal sulfide catalyst particles have a pore volume of at least 0.05 mL/g (e.g., 0.05 to 5 mL/g, 0.1 to 5 mL/g, 0.1 to 4 mL/g, 0.1 to 0.3 mL/g, or 0.1 to 2 mL/g), as determined by $N_2$ adsorption.

In one embodiment, the self-supported mixed metal sulfide catalyst particles have a mean particle diameter of at least 0.05 μm (e.g., 0.1 to 50 μm, or 0.5 to 50 μm).

Ring Opening

As discussed, the present self-supported mixed metal sulfide catalyst is useful in upgrading petroleum feed streams. Accordingly, a feed stream which is to be contacted with the self-supported mixed metal sulfide catalyst will typically contain a mix of hydrocarbons having one or more of the naphthenic ring-containing compositions, and the naphthenic ring-containing compositions may contain at least one alkyl substituent of 1 to 20 carbon atoms. The feed stream may comprise at least 5 wt. % (e.g., at least 25 wt.

%, at least 50 wt. %, 5 to 85 wt. %, 25 to 85 wt. %, or 50 to 85 wt. %) of at least one naphthenic ring-containing compound.

The hydrocarbon containing naphthene ring compositions that are to be opened may include $C_5$ and $C_6$ naphthene ring compounds that do not include additional ring members. Examples of these compounds include alkyl-substituted $C_5$ and $C_6$ naphthenes such as methylcyclopentanes, ethylcyclopentanes, propylcyclopentanes, butylcyclopentanes, pentylcyclopentanes, methylcyclohexanes, ethylcyclohexanes, propylcyclohexanes, butylcyclohexanes, and pentylcyclohexanes.

Naphthenic ring-containing compounds are found in a wide range of hydrocarbon feeds, such as petroleum streams boiling in the distillate range. These streams will typically include a variety of chemical compounds, including multi-ring compositions. A petroleum feed stream having a boiling point of from 175° C. to 600° C. may be used. Examples of such a feed stream include diesel fuel, jet fuel, heating oil, gas oil, and light cycle oil. Gas oil includes vacuum gas oil boiling in the range of from 340° C. to 565° C.

If significant aromatic compounds are present in the feed stream, it may be desirable to saturate them. The feedstock may contain less than 20 wt. % (e.g., less than 15 wt. %, or less than 10 wt. %) total aromatic compounds available for ring opening.

In some embodiments, a "sour" feed can be used. In such embodiments, the nitrogen content can be at least 50 wppm (e.g., at least 75 wppm or at least 100 wppm). Even in such "sour" embodiments, the nitrogen content can optionally but preferably be 2000 wppm or less (e.g., 1500 wppm or less or 1000 wppm or less). Additionally or alternatively in such "sour" embodiments, the sulfur content can be at least 100 wppm (e.g., at least 500 wppm or at least 1000 wppm). Further additionally or alternately, even in such "sour" embodiments, the sulfur content can optionally but preferably be 3.0 wt. % or less (e.g., 2.0 wt. % or less or 1.0 wt. % or less).

In some embodiments a "sweet" feed having a relatively lower level of sulfur and/or nitrogen contaminants may be used. A sweet feed can represent a hydrocarbon feedstock that has been hydrotreated and/or that otherwise can have a relatively low sulfur and nitrogen content. In such embodiments, the sulfur content can be 100 wppm or less (e.g., 50 wppm or less or 10 wppm or less). Additionally or alternatively in such embodiments, the nitrogen content can be 50 wppm or less (e.g., 25 wppm or less or 10 wppm or less).

To convert naphthene compounds to paraffins, a catalytically effective amount of the present self-supported mixed metal sulfide catalyst is contacted with an appropriate feed stream under catalytic ring opening conditions. The conditions are such that the $C_5$ and $C_6$ rings of the naphthene compounds are opened when contacted with the catalyst. Representative process conditions include temperatures of from 550° F. to 840° F. (288° C. to 449° C.), e.g., from 600° F. to 815° F. (343° C. to 435° C.); hydrogen partial pressures of from 250 to 5000 psig (1.8 to 34.6 MPa), e.g., from 500 to 3000 psig (3.5 to 20.9 MPa); liquid hourly space velocities of from 0.05 to 30 $h^{-1}$, e.g., from 0.5 to 5 $h^{-1}$; and hydrogen treat gas rates of from 200 to 10,000 SCF/B (35.6 to 1781 $rr^3/m^3$), e.g., from 1200 to 6000 SCF/B (213 to 1068 $rr^3/m^3$).

Conventional catalytic ring opening reactors may be used in the process disclosed herein. A fixed bed reactor system may be used wherein the feedstock is passed over one or more stationary beds of catalyst. Multiple reactors can be used in either series or parallel configurations.

Hydrogen gas conducted to the reaction process may flow over the catalyst either in a direction concurrent or countercurrent with the feed stream. Hydrogen is supplied to saturate the carbons where ring opening occurs, and it is usually supplied in stoichiometric excess. The reactor effluent may be passed to a separation zone where hydrogen that has not been consumed in the reaction process can be separated off and recycled to the reaction zone together with make-up hydrogen as needed or cascaded to a lower pressure unit for further processing.

The ring-opened product has increased linear paraffin functionality relative to that of the feed stream. The ring opened product may be recovered after the final processing step (i.e., after ring opening) or after any further optional treatment step (e.g., dewaxing, hydrofinishing), according to conventional methods. The recovered product may be used directly, for example, as a diesel fuel, jet fuel, gas oil, and heating oil, and it may be blended with other petroleum products and used as a diesel fuel, jet fuel, gas oil, and heating oil. When blended, the ring-opened product may be blended with a petroleum stream having a boiling point ranging from 175° C. to 600° C., wherein the blend has a cetane number of at least 40.

As a result of ring opening, the ring-opened product may have a lower boiling point, lower specific gravity, and/or lower aromatics content relative to that of the feed stream. For example, the ring-opened product may an overall reduction in total aromatics content of at least 10%, (e.g., at least 20%, at least 30%, at least 40%, at least 50%, at least 60%, at least 70%, at least 80%, at least 90%, or at least 95%), based on the feedstock composition.

EXAMPLES

The following illustrative examples are intended to be non-limiting.

Example 1

Ni—Mo—W Maleate Catalyst Precursor

Ammonium heptamolybdate (324 g) was dissolved in deionized water (2.3 kg). Ammonium metatungstate (1.39 kg) was dissolved in deionized water (1.5 kg). The two solutions were mixed together with stirring and pH maintained in the range of 9-10 by the addition of ammonium hydroxide.

A nickel nitrate solution was prepared by dissolving nickel nitrate hexahydrate (3.5 kg) in deionized water (1.9 kg) and then diluting with 6 kg of deionized water. A nickel sulfate solution was prepared by dissolving 244 g of nickel sulfate in 1.8 kg of deionized water. The nickel nitrate and nickel sulfate solutions were combined. Concentrated sulfuric acid (120 g) was added to the nickel solution followed by a solution of maleic acid (185 g) in water (460 g).

The solution of nickel nitrate, nickel sulfate, and maleic acid was then combined with the ammonium molybdate/ammonium metatungstate solution with stirring. The resulting slurry was heated at about 80° C. for 4 hours. Ammonium hydroxide was added as needed to maintain the pH at 6-7. The slurry was then filtered, and collected precipitate vacuum dried at room temperature overnight. The material was then dried at 120° C. for 12 hours.

The resulting material has a typical XRD pattern with a broad peak at 2.5 Å, denoting an amorphous Ni—OH containing material.

The resulting catalyst precursor had the following composition:
Ni: 63 mol %; Mo: 8 mol %; W: 29 mol %

Example 2

Ni—Mo—W Maleate Catalyst Precursor

This catalyst precursor was prepared in a manner similar to that of Example 1 except that the resulting catalyst precursor had the following composition:
Ni: 66 mol %; Mo: 15 mol %; W: 19 mol %

Example 3

Ni—Mo—W Maleate Catalyst Precursor

This catalyst was prepared in a manner similar to that of Example 1 except that the resulting catalyst precursor had the following composition:
Ni: 66 mol %; Mo: 10 mol %; W: 24 mol %

Example 4

Extrusion of Catalyst Precursor

Dried catalyst precursor (40 g) was mixed with METHOCEL™ cellulose ether (0.8 g) from Dow Chemical Company and deionized water (7 g) was added to this mixture. Additional deionized water (7 g) was added until the mixture was of an extrudable consistency. The mixture was then extruded and dried under $N_2$ at 120° C. prior to sulfiding.

Example 5

Sulfidation

The extrudates were shortened to an L/D of 1-2 and packed in ¾ inch tubular reactors. A total volume of 6 mL catalyst was used. The void spaces among catalyst extrudates were filled with 100 mesh as interstitial to improve contacting and prevent channeling.

Catalyst sulfiding was conducted following a liquid phase sulfiding procedure wherein a straight run diesel feed containing 2.5 wt. % dimethyl disulfide (DMDS) was used as a sulfiding agent. Sulfiding of the catalyst precursor occurred in two steps: a 400° F. to 500° F. low temperature sulfiding step followed by a 600° F. to 700° F. high temperature sulfiding. After sulfidation, the total pressure was increased to 2000 psig and the feed changed over to the straight run diesel to line out the catalyst system for three days. The CAT temperature was then raised to the desired target temperature.

Example 6

Catalytic Performance

Catalysts were evaluated using an unconverted oil (UCO), a high boiling hydrocarbon fraction separated from a hydrocracker effluent, and its blends with dimethyl disulfide (DMDS) and/or tributylamine ($Bu_3N$). The properties of the UCO feed are listed in Table 1.

Reaction conditions included a total pressure of 2000 psig, a liquid hourly space velocity of 1.5 $h^{-1}$, and a hydrogen treat gas rate of 5000 SCF/B.

TABLE 1

| | |
|---|---|
| API Gravity | 31.0 |
| Sulfur, ppm wt. % | 5.78 |
| Nitrogen, ppm wt. % | 1.28 |
| Hydrogen, wt. % | 13.75 |
| Pour Point, ° C. | 41.0 |
| PCI | 150 |
| Hydrocarbon Type (Analysis by Mass Spectrometry) | |
| Paraffins, LV % | 22.4 |
| Naphthenes, LV % | 64.5 |
| Aromatics, LV % | 13.1 |
| VI | 118 |
| $KV_{100}$, $mm^2/s$ | 5.816 |
| $KV_{70}$, $mm^2/s$ | 11.90 |
| Simulated Distillation, wt. %-° F. (ASTM D2887) | |
| 0.5/5 | 525/638 |
| 10/30 | 685/767 |
| 50/ | 822 |
| 70/90 | 884/973 |
| 95/99.5 | 1008/1080 |
| 700° F.-, wt. % | 12.3 |

Table 2 summarizes C—C bond cleavage activity for the catalysts as measured by the cracking conversion and aromatics content in products.

TABLE 2

| Catalyst Combination (Ni/Mo/W, mol %) | Feed | CAT, ° F. | HCR Conversion (<700° F.), wt. % | Aromatics, wt. % |
|---|---|---|---|---|
| 63/8/29 | UCO | 720 | 15.0 | 5.1 |
| 63/8/29 | UCO/1.5 wt. % DMDS | 720 | 11.8 | 6.0 |
| 63/8/29 | UCO/1.5 wt. % DMDS/ 0.1 wt. % $Bu_3N$ | 720 | 9.9 | 6.8 |
| 63/8/29 | UCO/2.5 wt. % DMDS/ 0.1 wt. % $Bu_3N$ | 720 | 6.3 | 7.3 |
| 66/15/19 | UCO | 720 | 14.3 | 6.0 |
| 66/10/24 | UCO | 720 | 18.2 | 4.8 |
| 66/10/24 | UCO/1.5 wt. % DMDS/ 0.1 wt. % $Bu_3N$ | 720 | 25.4 | 3.8 |
| 66/10/24 | UCO | 760 | 19.0 | 11.7 |
| 66/10/24 | UCO/1.5 wt. % DMDS/ 0.1 wt. % $Bu_3N$ | 760 | 30.5 | 9.3 |

As shown in the Table 2, the self-supported mixed metal sulfide catalyst having a W/Mo molar ratio of about 2.4 exhibited superior C—C bond cleavage activity. Surprisingly, C—C bond cleavage is promoted in the presence of sulfur and/or nitrogen.

The invention claimed is:

1. A process for selective opening naphthene rings of naphthene ring-containing compounds in a feed stream, the process comprising:
   contacting a naphthene ring-containing feed stream under ring opening conditions with hydrogen and a self-supported mixed metal sulfide catalyst comprising nickel sulfide, molybdenum sulfide, tungsten sulfide and an organic complexing agent, thereby forming a ring-opened product having increased linear paraffin functionality relative to that of the naphthene ring-containing feed stream;
   wherein the self-supported mixed metal sulfide catalyst is characterized as having a composition of metal components, in terms of molar ratios, as follows:
   (a) 0.25≤Ni/(Ni+Mo+W)≤0.80;
   (b) 0<Mo/(Ni+Mo+W)≤125;

(c) 0.12≤W/(Ni+Mo+W)≤0.50; and
(d) 1.5<W/Mo<3.0,
wherein the organic complexing agent is maleic acid.

2. The process of claim 1, wherein the naphthene ring-containing feed stream has a nitrogen content of at least 50 wppm and a sulfur content of at least 100 wppm.

3. The process of claim 1, wherein the ring opening conditions include a temperature of from 550° F. to 840° F. (288° C. to 449° C.); a hydrogen partial pressure of from 250 to 5000 psig (1.8 to 34.6 MPa); a liquid hourly space velocity of from 0.05 to 10 h$^{-1}$; and a hydrogen treat gas rate of from 200 to 10,000 SCFB (35.6 to 1781 m$^3$/m$^3$).

4. The process of claim 1, further comprising recovering the ring-opened product.

5. The process of claim 4, further comprising blending the ring-opened product with a petroleum stream having a boiling point from 175° C. to 600° C., wherein a blend of the ring-opened product and the petroleum stream has a cetane number of at least 40.

6. The process of claim 1, wherein the self-supported mixed metal sulfide catalyst is binderless.

7. The process of claim 1, wherein the self-supported mixed metal sulfide catalyst is non-calcined.

8. The process of claim 1, wherein the W/Mo molar ratio is in a range of 2.0 to 2.8.

9. The process of claim 1, wherein the self-supported mixed metal sulfide catalyst is characterized as having a molar ratio of metal components Ni, Mo and W in a range of:

(a) 1.08≤Ni/(Mo+W)≤2.03;
(b) 0<Mo/(Ni+W)≤0.18; and
(c) 0.20≤W/(Ni+Mo)≤0.72.

10. The process of claim 1, wherein the self-supported mixed metal sulfide catalyst has a multi-phased structure comprising five phases: (1) a molybdenum sulfide phase; (2) a tungsten sulfide phase; (3) a molybdenum tungsten sulfide phase; (4) an active nickel phase; and (5) a nickel sulfide phase.

11. The process of claim 10, wherein the molybdenum tungsten sulfide phase comprises at least a layer, and wherein the at least a layer contains at least one of:

(a) molybdenum sulfide and tungsten sulfide; (b) tungsten isomorphously substituted into molybdenum sulfide as individual atoms or as tungsten sulfide domains; (c) molybdenum isomorphously substituted into tungsten sulfide as individual atoms or as molybdenum sulfide domains; and (d) combinations thereof.

12. The process of claim 10, wherein the active nickel phase comprises at least one of atomic nickel and reduced nickel substituted into the molybdenum tungsten sulfide phase.

13. The process of claim 10, wherein the nickel sulfide phase comprises slabs of at least one of Ni$_9$S$_8$ and Ni$_3$S$_2$ crystals.

* * * * *